United States Patent
Philipp et al.

(10) Patent No.: US 7,810,371 B2
(45) Date of Patent: Oct. 12, 2010

(54) PROCESS AND ARRANGEMENT FOR CALIBRATING AND/OR EQUILIBRATING SINGLE-CHANNEL AND MULTI-CHANNEL LIQUID HANDLING DEVICES

(75) Inventors: Dirk Philipp, Veilsdorf (DE); Torsten Rausch, Dingsleben (DE)

(73) Assignee: CyBio AG, Jena (DE)

( * ) Notice: Subject to any disclaimer, the term of this patent is extended or adjusted under 35 U.S.C. 154(b) by 504 days.

(21) Appl. No.: 11/867,139

(22) Filed: Oct. 4, 2007

(65) Prior Publication Data

US 2008/0083263 A1    Apr. 10, 2008

(30) Foreign Application Priority Data

Oct. 5, 2006  (DE) .................... 10 2006 047 754
Feb. 27, 2007  (DE) .................... 10 2007 010 345

(51) Int. Cl.
 *G01F 19/00*  (2006.01)
(52) U.S. Cl. ...................................... 73/1.74
(58) Field of Classification Search .................... 73/1.74
See application file for complete search history.

(56) References Cited

U.S. PATENT DOCUMENTS

| | | | |
|---|---|---|---|
| 4,888,718 A | 12/1989 | Furuse | |
| 6,993,966 B2 | 2/2006 | Stenmark | |
| 7,197,948 B2 * | 4/2007 | Sander | 73/863.01 |
| 2006/0272387 A1 * | 12/2006 | Klosterman et al. | 73/1.74 |

FOREIGN PATENT DOCUMENTS

| | | |
|---|---|---|
| DE | 636 619 | 9/1936 |
| DE | 897 331 | 7/1949 |
| DE | 40 13 373 | 9/1991 |
| DE | 43 39 933 | 6/1994 |
| DE | 695 25 486 | 8/2002 |
| DE | 096 24 856 | 2/2005 |
| DE | 100 41 051 | 8/2006 |
| WO | 83/02321 | 7/1983 |
| WO | 00/73745 | 12/2000 |
| WO | 2006/009446 | 1/2006 |

OTHER PUBLICATIONS

Patent Abstract of Japan, Publication No. 62-207912 published Sep. 12, 1987 Suntory Ltd. "Method and Instrument for Measurement Volume of Container".

* cited by examiner

*Primary Examiner*—Robert R Raevis
(74) *Attorney, Agent, or Firm*—Frommer Lawrence & Haug LLP

(57) ABSTRACT

An arrangement and process for calibrating and/or equilibrating single-channel and multi-channel liquid handling devices, wherein a dispensing volume of a liquid is dispensed via the dispensing channels of a liquid handling device into a measurement chamber of a measurement chamber carrier, each measurement chamber being associated with a dispensing channel, and the individual measurement chambers are hermetically sealed successively relative to the environment and are connected to a pressure chamber under an operating pressure so that an equilibrium pressure occurs that is relevant to the respective dispensing volume.

10 Claims, 6 Drawing Sheets

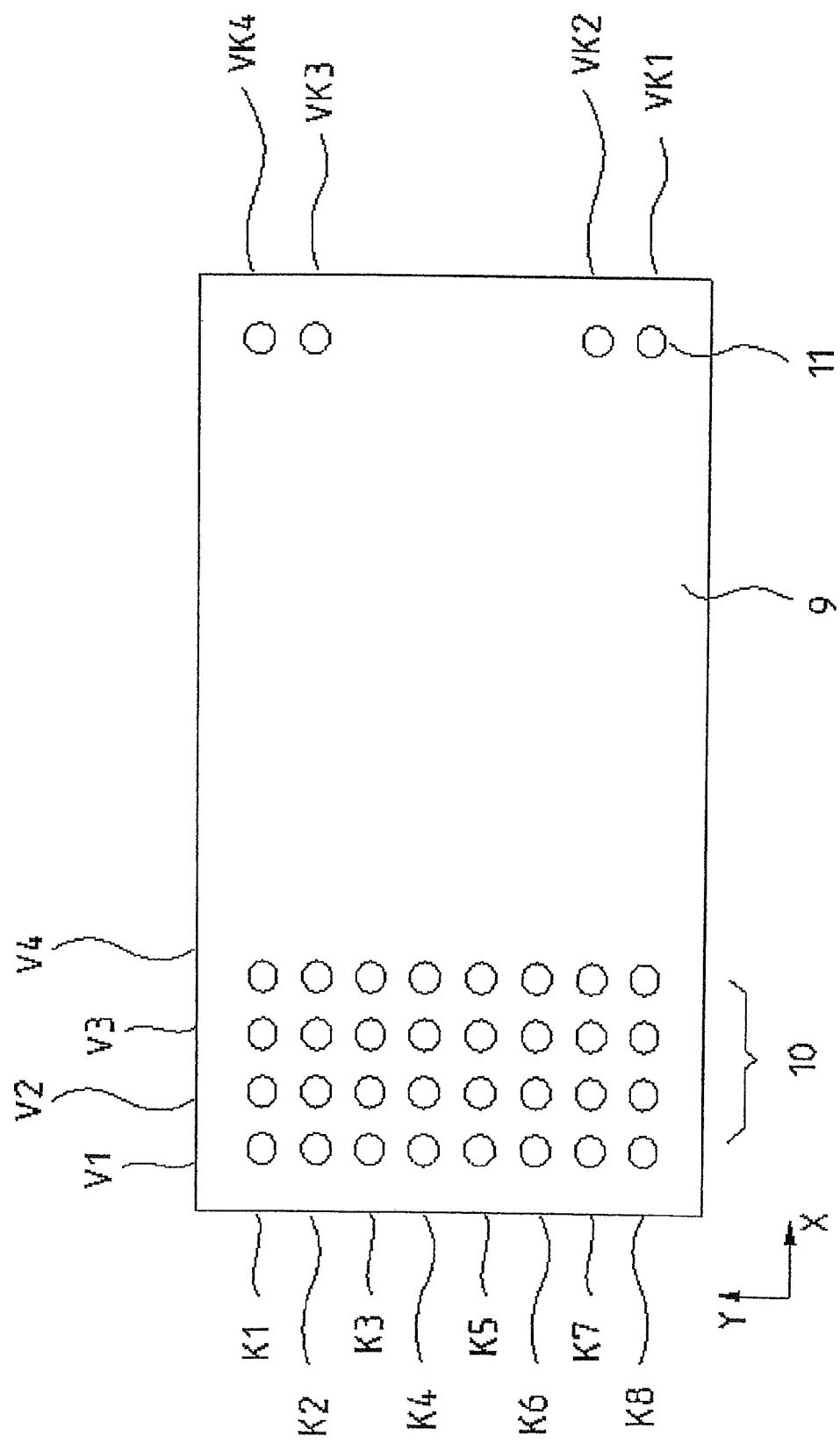

PROCESS AND ARRANGEMENT FOR CALIBRATING AND/OR EQUILIBRATING SINGLE-CHANNEL AND MULTI-CHANNEL LIQUID HANDLING DEVICES

CROSS-REFERENCE TO RELATED APPLICATIONS

This application claims priority of German Application No. 10 2006 047 754.5, filed Oct. 5, 2006 and German Application No. 10 2007 010 345.1, filed Feb. 27, 2007, the complete disclosures of which are hereby incorporated by reference.

BACKGROUND OF THE INVENTION a) Field of the Invention

By single-channel and multi-channel liquid handling devices is meant in the following both dispensing devices and pipetting devices with one or more dispensing channels by which a liquid can be dispensed simultaneously, particularly in the microliter range and nanoliter range. Broadly speaking, this also includes devices and arrangements which dispense dosed liquid in the processing and manufacturing industries.

b) Description of the Related Art

Devices of the type mentioned above are used particularly for analyzing liquids, e.g., for medical diagnosis and for searching pharmaceutical active substances, where the tendency is toward increasingly smaller measurement volumes which can be handled simultaneously in increasing quantities.

It is required for reproducible analysis results that the individual dispensing volumes do not deviate from a predetermined reference value beyond a predetermined tolerance range and, much more importantly, that they do not deviate from one another beyond a predetermined tolerance range.

In the prior art, in order to maintain these tolerances, the passive components determining the dispensing volumes are correspondingly selected and paired so that identical volumes (within the predetermined tolerance range) are dispensed under identical control parameters.

In addition, or alternatively, by changing the dispensing parameters identical dispensing volumes can be achieved by calibrating the dispensing channels (matching the individual values to a reference value) or equilibrating the dispensing channels (matching the individual values of the channels to one another).

Volume measurement, as is required for the calibration and/or equilibration of liquid handling devices, can be achieved principally by measurement of volume, mass or flow. The predominant principle of measurement for measuring volumes in cells, microtitration plates, or the like optical transparent devices is photometric measurement, whereas gravimetry and calorimetry are predominantly used for determining mass and flow, respectively. An auxiliary liquid with correspondingly suitable optical characteristics is often used on the assumption that the original liquid behaves in like manner with respect to its fluid characteristics.

In photometric methods, a photometric equivalent (reader factor) between the photometric measurement (absorbance, fluorescence) and the volumes of liquid must always be furnished as a reference for accuracy. This is usually carried out using a laboratory scale. For this purpose, the density of the liquid must also be known and may not vary. This value is dependent upon the photometric characteristics of the liquid (dye solution) and the geometry of the vessel (fill level, meniscus, vessel opening, vessel material, etc.). This equivalent must be recalculated whenever the type of plate or vessel is changed or when using a different dye solution (necessary for measuring a different volume).

In a process according to the invention, this can be dispensed entirely because calibration and/or equilibration can be carried out with the liquid used in subsequent operations, while the photometric characteristics of the liquid and measurement chambers have no relevance.

In photometric methods, special precautions must be taken with respect to evaporation because of the required mixing times (diffusion time: 30-60 minutes). When microtiter plates are used as vessels, various methods are employed for reducing evaporation. Masking with a foil (seal) and an ambient atmosphere saturated by the corresponding liquid are known.

On the other hand, the measuring time in a process according to the invention is shorter because no mixing time is required and, therefore, evaporation has less influence. Naturally, a small vessel opening and a saturated ambient atmosphere are also advantageous.

Evaporation can be reduced by means of an advantageous shaping of the vessels.

The influence of surface effects is increased by reducing the volumes and, therefore, the geometric dimensioning of the vessels in which the volumes are to be measured. In this connection, the formation of menisci, acting capillary forces and the wetting behavior must be taken into account. With very small volumes, evaporation becomes a critical factor. As measurement volumes become increasingly smaller in the known measurement methods, measurement errors become larger as a result of these surface effects so that the known measurement methods appear to be poorly suited to calibration and/or equilibration of liquid handling devices dispensing very small volumes.

OBJECT AND SUMMARY OF THE INVENTION

It is the primary object of the invention to provide a process and an arrangement by which the liquid handling devices can be calibrated and/or equilibrated with high accuracy.

This object is met for a process for calibrating and/or equilibrating single-channel and multi-channel liquid handling devices, in accordance with the invention, in which a dispensing volume of a liquid is dispensed in a measurement chamber of a measurement chamber carrier via dispensing channels of the liquid handling device, each measurement chamber being associated with a dispensing channel, and the dispensing volumes which correspond in each instance to an actual volume are determined in the individual measurement chambers and compared to a reference volume and/or to one another in order to change the device parameters influencing the respective dispensing volume in the event of deviations beyond a predetermined tolerance limit, comprising the following process steps:

generating an operating pressure in a pressure chamber whose volume is known;

hermetically sealing an unfilled measurement chamber and connecting the measurement chamber to the pressure chamber;

measuring the chamber pressure, which is now equal to a first equilibrium pressure that has undergone a pressure change relative to the operating pressure depending on the measurement chamber volume;

storing the first equilibrium pressure associated with this measurement chamber;

opening the measurement chamber and repeating the preceding process steps depending on the quantity of additional measurement chambers in the measurement chamber carrier;

filling the measurement chambers by dispensing a liquid via the dispensing channels of the liquid handling device;

generating the operating pressure in the pressure chamber;

hermetically sealing a measurement chamber and connecting this measurement chamber to the pressure chamber;

measuring the chamber pressure, which is now equal to a second equilibrium pressure that has undergone a pressure change relative to the operating pressure depending on the difference between the measurement chamber volume and the liquid volume;

storing the second equilibrium pressure associated with this measurement chamber;

opening the measurement chamber and repeating the preceding three process steps depending on the quantity of additional measurement chambers in the measurement chamber carrier;

determining difference values between the first and second equilibrium pressures associated in each instance with a measurement chamber;

associating individual actual volume values with the individual difference values using the thermal equation of states of ideal gases $p \cdot V = n \cdot R \cdot T$, where p is pressure, V is volume, T is temperature, and R is the universal gas constant, and the proposition that the amount of gas in the system before and after the pressure equilibrium is constant, i.e., the amount of gas in the measurement chamber plus the amount in the pressure chamber is equal to the amount in the pressure chamber and measurement chamber after equilibrium;

comparing these actual volume values in each instance to a value for a reference volume and/or to one another; and changing the device parameters of the liquid handling device influencing the dispensing volumes are changed in the event of deviations of the actual volume values from the value for the reference volume or from one another beyond a predetermined tolerance and, if necessary, repeating the preceding process steps beginning with the filling of the measurement chambers.

Also in accordance with the invention, the object is met in an arrangement for calibrating and/or equilibrating single-channel and multi-channel liquid handling devices comprising:

a measurement chamber carrier having one or more measurement chambers with openings on one side and arranged in a grid;

each of the openings lying in a plane and where grid spacing is adapted, if necessary, to grid spacing of the dispensing channels of the liquid handling device to be calibrated and/or equilibrated; and a storing and evaluating unit in which relevant measurement values for the dispensing volumes of a liquid dispensed to the measurement chambers via the dispensing channels corresponding in each instance to an actual volume are formed so as to be associated with the measurement chambers and stored and compared to a value for reference volumes and/or to one another in order to determine tolerance deviations of the dispensing volumes, and a control unit which is connected to the storing and evaluating unit for changing influential device parameters if necessary; and further comprising:

a pressure chamber being provided and being connected on the input side by a first pressure line to a device for generating an operating pressure and communicating on an output side by a second pressure line with a seal which surrounds the free end of the pressure line;

an inlet valve being provided for opening and closing the first pressure line and an outlet valve being provided for opening and closing the second pressure line;

a pressure sensor by which the chamber pressure in the pressure chamber can be measured being connected to the pressure chamber;

a holder being provided in which the measurement chamber carrier is arranged in a horizontal and vertical position defined in relation to the seal, and a sealing surface of the seal lying parallel to the plane of the opening of the measurement chambers, which sealing surface is larger than the opening of a measurement chamber;

means for horizontal relative movement between the measurement chamber carrier and the seal being provided to position the measurement chambers successively beneath the seal;

means for the vertical relative movement between the measurement chamber carrier being arranged in the holder and the seal being provided to periodically hermetically seal a measurement chamber located beneath the seal relative to the environment and to connect the measurement chamber to the pressure chamber; and said pressure sensor and said means for relative movement being connected to the storing and evaluating unit.

It is essential to the invention that the dispensing volume of a liquid in a measurement chamber with an unknown measurement chamber volume is determined by measuring and evaluating pressure changes in a gas. Accordingly, the process, by reason of its principle, is not dependent on any surface effects, gas inclusions, contamination, or the like.

As a basic principle, different types of liquid handling devices can be calibrated and/or equilibrated by means of the arrangement according to the invention. For this purpose, it must be possible to change the dispensing behavior of the device, i.e., the dispensing volumes of its individual dispensing channels.

Basically, the possibilities are as follows:

a) Systems whose dispensing volumes depend on changing the lift (single-channel and multi-channel pipettes; pump systems with variable reciprocating plunger pumps, etc.). In this case, the displacement of the liquid dispensing medium can be carried out by a gas (air displacement) or a liquid/solid (positive displacement).

b) Systems whose dispensing volumes depend on the opening time of the liquid channel (pressure-actuated systems with a dosing valve). Here also, the displacement of the liquid dispensing medium can be carried out by a gas, a liquid or a solid.

c) Systems whose dispensing volumes are determined by the delivery time of the system (hose pumps, diaphragm pumps, micropump systems, piezo-dispensers).

d) Systems whose delivery rates (flow) can be manipulated (pumps, micropump systems, piezo-dispensers).

e) Systems which accumulate incremental (known) volumes (piezo-dispensers, bubble jets, very small droplets, etc.). The quantity of individual dispensed volumes determines the dispensing volumes (dispensing volume=quantity of volumes×incremental volume; E.g., to dispense 50 µl with a system which can dispense only 1 µl, the dispensing process must be repeated fifty times).

The invention will be described more fully in the following with reference to an embodiment example shown in the drawings.

BRIEF DESCRIPTION OF THE DRAWINGS

In the drawings:

FIG. 2b is a top view of a measurement chamber carrier;

DESCRIPTION OF THE PREFERRED EMBODIMENTS

Figure 1A:
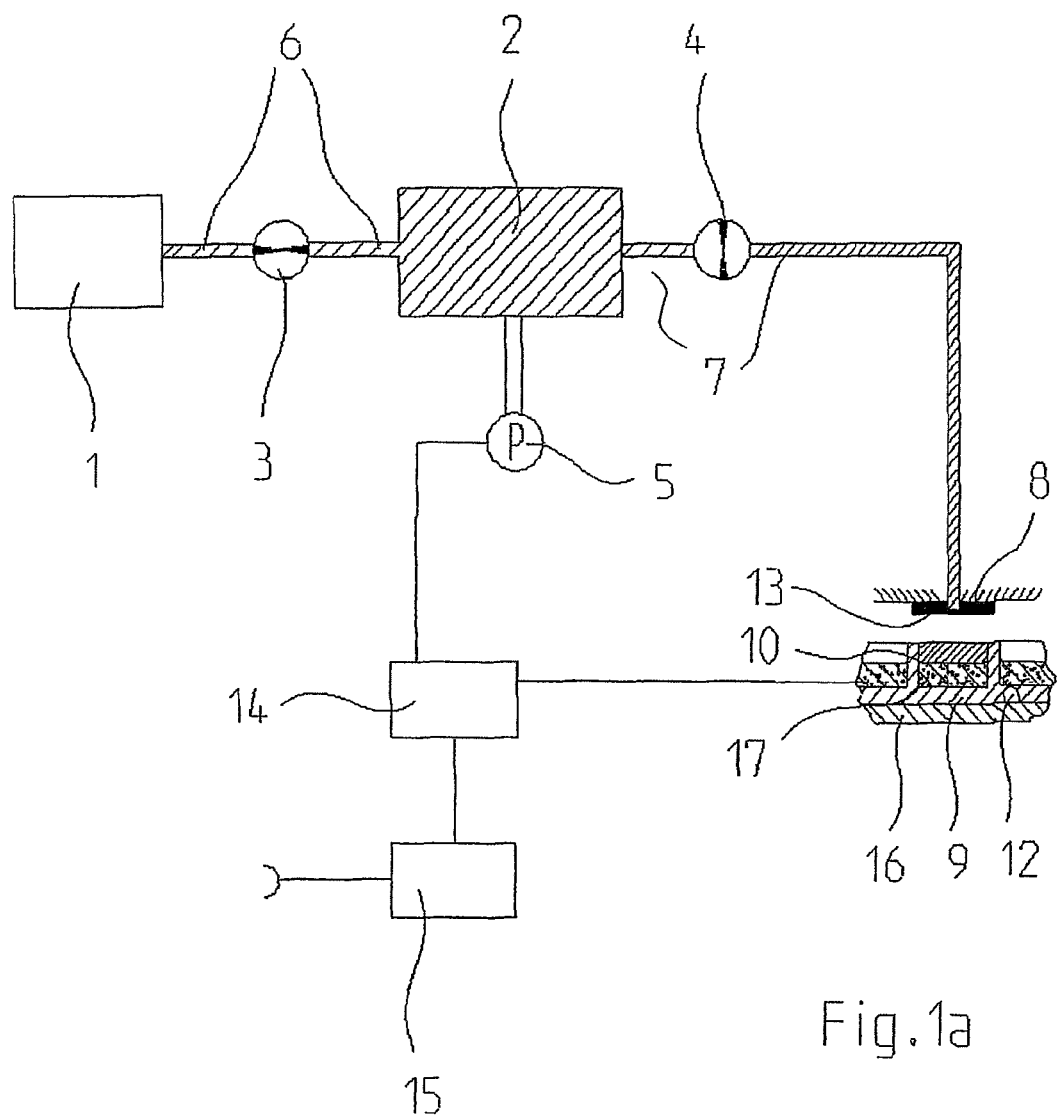
FIG. 1a shows a schematic view of an arrangement according to the invention with an open measurement chamber.
Figure 1B:
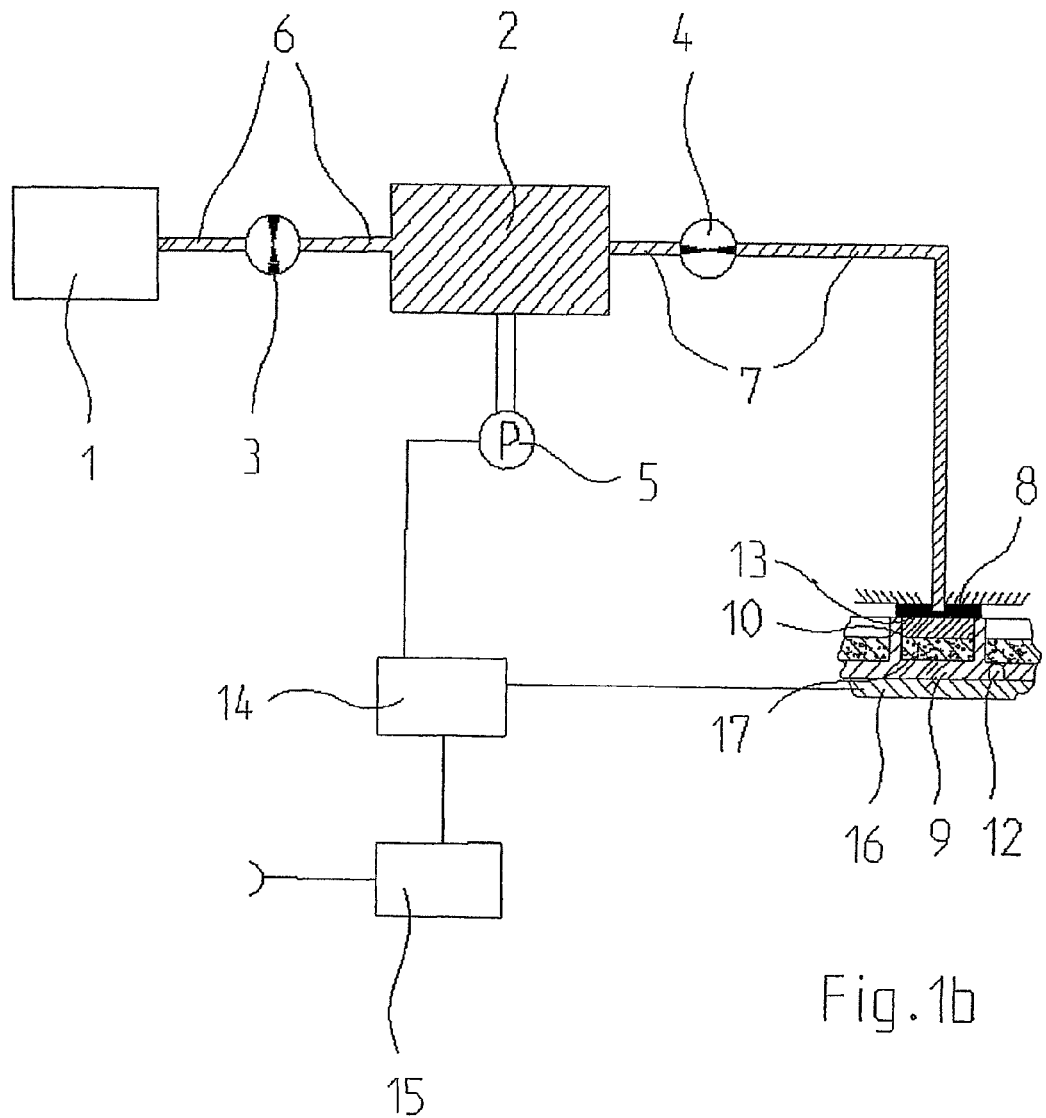
FIG. 1b shows a schematic view of an arrangement according to FIG. 1a with a closed measurement chamber.

An arrangement according to the invention (FIGS. 1a, 1b) substantially comprises a device for generating an operating pressure 1 which is connected on the input side to a pressure chamber 2 by a first pressure line 6, a second pressure line 7 which is connected on the output side to the pressure chamber 2, a seal 8 being fitted to its free end so as to enclose this end, an input valve 3, an output valve 4 for selectively opening and closing the pressure lines 6, 7, a pressure sensor 5 connected to the pressure chamber 2, and a holder 12 for a measurement chamber carrier 9.

Figure 2A:
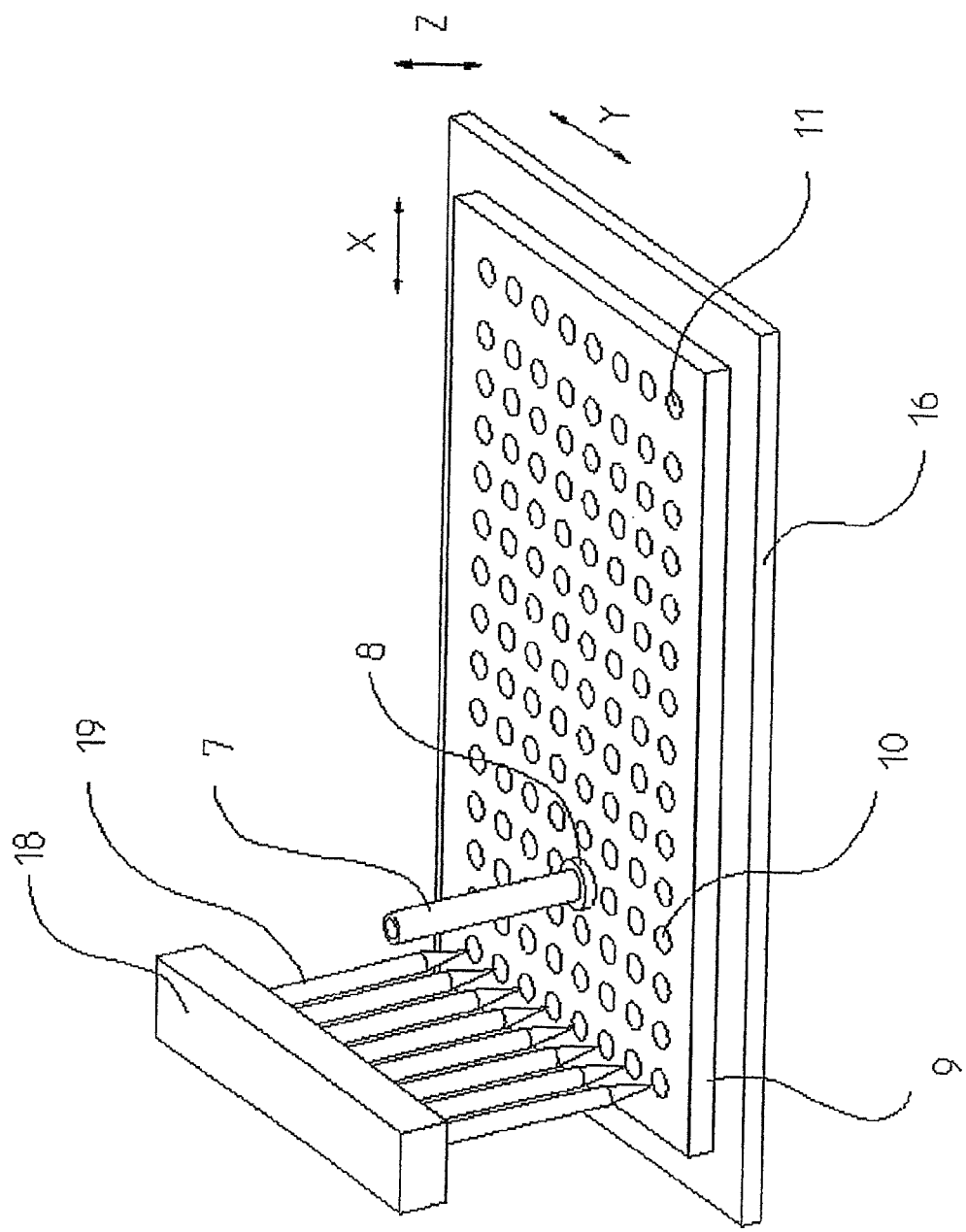
FIG. 2a shows a measurement chamber carrier on a 3D coordinate table.

The measurement chamber carrier 9 comprises one or more measurement chambers 10 which are open on one side (FIGS. 2a, 2b).

A measurement chamber carrier 9 with only one measurement chamber 10 can be used to calibrate a single-channel liquid handling device 18. Naturally, there is no grid spacing here as there is in multi-channel liquid handling devices 18 and measurement chamber carriers 9 with a plurality of measurement chambers 10.

In order to calibrate a multi-channel liquid handling device 18, the measurement chamber carrier 9 must have at least a quantity of measurement chambers 10 identical to the quantity of dispensing channels 19 in the multi-channel liquid handling device 18, preferably an integral multiple of the quantity of measurement chambers 10. Further, the measurement chambers 10 must be arranged relative to one another in a grid spacing that is adapted to the grid spacing of the dispensing channels 19 so that each dispensing volume is received by a measurement chamber 10 in one dispensing cycle in which a dispensing volume is dispensed to all of the dispensing channels 19 simultaneously. It is important for the process according to the invention and the arrangement according to the invention that the openings of the measurement chambers 10 which are open on one side, or more exactly the rim area defining the openings, lie in a plane, preferably in a common plane.

The openings must lie in a plane so that they can be hermetically sealed by the seal 8 which comes into contact with them and which has a sealing surface 13. It is advantageous when all of the openings lie in the same plane because then the required vertical movement, which will be described in more detail in connection with the description of the method process, proceeds along a constant path.

It is compulsory that the seal 8 be larger than the openings of the measurement chambers 10 so that the seal 8 can seal the measurement chambers 10 from the environment.

The holding volumes of the individual measurement chambers 10 need not be identical or known.

In principle, all open vessel systems may be used as measurement chamber carriers 9 with measurement chambers 10. The measurement chamber carrier 9 can be a special carrier outfitted with individual vessels, or the individual vessels are integrated in the measurement chamber carrier 9. Microtitration plates and cell arrangements or tube racks which are reusable or provided for onetime use (disposable) can be used in particular. The measurement chamber carrier 9 with measurement chambers 10 can also be reduced to a single vessel. The use of microtitration plates as measurement chamber carriers 9 or the use of measurement chamber carriers 9 in the format of a microtitration plate has the advantage that the measurement chamber carrier 9 can be used with the usual peripheral devices for handling microtiter plates such as stackers, manipulators, transport sleds, and robotic gripping devices for handling the measurement chamber carriers 9.

When reusable measurement chambers 10 are used, the process according to the invention can be made faster by detecting and storing the volumes of the empty measurement chambers 10 only once the first time the process is carried out.

It is advantageous when reference chambers 11 are provided in the measurement chamber carrier 9 in addition to the actual measurement chambers 10, where the volumes of the reference chambers 11 are known so that it is possible to calibrate the arrangement immediately at the start of the process under process conditions identical to those under which the calibrating and/or equilibrating process of the liquid handling device 18 is carried out. The reference chambers 11 can also be located on a separate carrier.

The holder 12, which is formed by two dowel pins engaging in the base of the measurement chamber carrier 9 in the embodiment example described herein, serves to position the measurement chamber carrier 9 relative to the seal 8 in a defined, reproducible manner. In principle, the holder 12 can be formed by any positively engaging or frictionally engaging holder instead of by the above-mentioned dowel pins.

The seal 8 is advantageously arranged in a stationary manner at a housing part of the arrangement, and the necessary relative movements between the measurement chamber carrier 9 and the seal 8 are carried out by a 3D coordinate table on which the measurement chamber carrier 9 is fixed by the holder 12.

It will be clear to the person skilled in the art that both the holder 12 and therefore the measurement chamber carrier 9 can be stationary and the seal 8 can be constructed so as to be movable in three dimensions relative to the measurement chamber carrier 9 by means of a displacement mechanism. Combined variants in which, e.g., the measurement chamber carrier 9 can be displaced in a horizontal plane and the seal 8 is moved vertically up and down are also possible.

Instead of a pressure sensor 5 produced, e.g., by microtechnology, the pressure difference can also be determined, e.g., by flow measurement by means of optoelectronic or electric sensors in a capillary.

In addition to the structural component parts and assemblies mentioned above, the arrangement also comprises a storing and evaluating unit 14 which is connected to the 3D coordinate table 16 and to the pressure sensor 5. The storing and evaluating unit 14 receives the coordinates of the respective measurement chamber 10 positioned under the seal 8 from the 3D coordinate table 16 and receives the measurement values relevant for this measurement chamber 10 from the pressure sensor 5 and can evaluate these measurement values in a suitable manner and associate them with an actual volume.

The arrangement also advantageously comprises a control unit 15 which is connected to the storing and evaluating unit 14 and which has an interface for the liquid handling device 18 to be calibrated and/or equilibrated, which enables an automatically controlled change of the parameters of the liquid handling device 18 which influence the dispensing of volumes.

The volume of the pressure chamber 2 and of the pressure lines 6, 7 is known and is stable over the changes in pressure inherent to the process.

The arrangement, with the exception of the 3D coordinate table, can be enclosed along with the holder 12 and the measurement chamber carrier 9 held in the latter, but the seal 8 must be accessible from the outside. Other individual component units such as the device for generating an operating pressure 1 could also be arranged outside the housing.

The arrangement can be arranged and used as an individual unit or integrated in a chain of intercommunicating laboratory devices or in one laboratory device.

Before the start of the process, a measurement chamber carrier 9 suitable for the liquid handling device 18 to be calibrated and/or equilibrated is selected and positioned on the 3D coordinate table 16 in the holder 12.

A measurement chamber carrier 9 suitable for a liquid handling device 18 with, e.g., eight dispensing channels 19, could look like that illustrated in FIG. 2b. For example, with four dispensing cycles of specifically different reference volumes V1-V4, the liquid handling device 18 can fill the measurement chambers 10 by means of its eight dispensing channels 19.

The terms dispensing volume, actual volume, reference volume V1-V4 and calibrating volume VK1-VK4 are used for the following description. By reference volume V1-V4 is meant the dispensing volume which is to be dispensed by a dispensing channel. In general, the volume actually dispensed deviates from the reference volume V1-V4 and is referred to as the actual volume. The known dispensing volume for calibration is referred to as the calibrating volume VK1-VK4 and can advantageously be identical to a reference volume V1-V4.

The measurement chambers 10 (see FIG. 2b) present in a row in x-direction are measurement chambers K1-K8 which are each allocated to a dispensing channel 19 and which are filled successively through the same dispensing channel 19 with actual volumes which generally deviate from the different reference volumes V1-V4.

On the other hand, the measurement chambers 10 in a row in y-direction are filled simultaneously by different dispensing channels 19 and, accordingly, by different actual volumes in spite of the fact that an identical reference volume is dispensed per dispensing cycle V1-V4.

According to the example, the measurement chambers 10 in x-direction are filled with different reference volumes V1-V4 over four successive dispensing cycles. These reference volumes V1-V4 advantageously correspond to the calibrating volumes VK1-VK4 with which the arrangement is calibrated by means of reference chambers 11 which will be described more fully in the following.

The determination of the deviation of the actual volumes from one another and from the reference volumes V1-V4 is required for the equilibration and calibration of the dispensing channels 19 and is the object of the arrangement.

For calibrating the arrangement it is advantageous when the measurement chamber carrier 9 has reference chambers 11. A quantity of two reference chambers 11 having either equal or different known measurement chamber volumes is sufficient in itself. With reference chambers 11 having equal measurement chamber volumes, e.g., in a microtitration plate, the calibration is carried out by means of one or two known calibrating volumes VK1-VK4, although this would require an independent measurement system for determining these calibrating volumes VK1-VK4.

With reference chambers 11 having different measurement chamber volumes, accomplished in particular by their varying depths, the arrangement can be calibrated without having to fill the reference chambers 11.

The measurement chamber volumes and calibrating volumes are advantageously tailored to the specific application, i.e., the arrangement is calibrated exactly to the reference volumes to be dispensed by the liquid handling device.

For example, when four different reference volumes are to be dispensed by the dispensing channels, it is advantageous when the measurement chamber carrier 9 has four reference chambers 11 whose measurement chamber volumes are individually known and which are practically filled with calibrating volumes VK1-VK4 corresponding to the four different reference volumes V1-V4 in order to calibrate the arrangement to these exact volumes.

After the measurement chamber carrier 9 has been selected and positioned on the 3D coordinate table 16 in a holder 12 intended for this purpose, the process can begin.

1st Process Step:

The output valve 4 is closed, the input valve 3 is opened, and a preselected operating pressure $P_{DK}$ of a gas is built up in the pressure chamber 2 whose volume $V_{DK}$ is known and which is now connected to the device for generating an operating pressure 1. The operating pressure $P_{DK}$ is preferably positive relative to the normal atmospheric pressure, which is known, but may also be negative. As soon as the operating pressure $P_{DK}$ occurs in the pressure chamber 2, which can be monitored by the pressure sensor 5, the input valve 3 is closed.

2nd Process Step:

The measurement chamber carrier 9 is positioned horizontally beneath the seal 8 in such a way that a first measurement chamber 10 comes to a stop in the center below the seal 8. The measurement chamber carrier 9 is now lifted vertically until the sealing surface 13 of the seal 8 tightly contacts the rim area of the measurement chamber 10, wherein the pressing force between the rim of the measurement chamber and the seal 8 must be greater than the operating pressure.

Process steps 1 and 2 may be carried out consecutively or simultaneously.

3rd Process Step:

After the above-mentioned process steps have been concluded, the output valve 4 is opened so that the gas flows into the measurement chamber 10 and a pressure equilibrium is brought about between the pressure chamber 2 and the sealed measurement chamber 10. The occurring equilibrium pressure $P_{equilibrium}$ (hereinafter: first equilibrium pressure), which is a measure of the chamber volume of this measurement chamber 10, is measured by means of the pressure sensor 5 and is stored so as to be associated with this measurement chamber 10. The data of the respective measurement chambers 10 which are identified by their position are received by the storing and evaluating unit 14 from the 3D coordinate table 16 which determines the respective table position, e.g., by means of an encoder.

4th Process Step:

The 3D coordinate table 16 is lowered so that the measurement chamber 10 is opened again. If the output valve 4 remains open, the pressure lines 6, 7 and the pressure chamber 2 are vented.

5th Process Step:

Process steps 1-4 are repeated insofar as there are still measurement chambers 10 in the measurement chamber carrier 9 that have not yet been measured.

6th Process Step:

After all of the measurement chambers 10 have been measured, they are filled with a liquid 17 in one or more dispensing cycles by the liquid handling device 18 to be calibrated and/or equilibrated, and process steps 1-6 are repeated. The equilibrium pressure now occurring (hereinafter: second equilibrium pressure) is a measure for the difference between the previously determined measurement chamber volumes and the respective dispensing volume (actual volume) of liquid 17 dispensed to the measurement chamber 10, so that the respective dispensing volume (actual volume) of the individual dispensing channels 10 may be calculated from this.

7th Process Step:

After all of the measurement values have been stored in the storing and evaluating unit 14 so as to be associated with the measurement chambers 10 and the values for the reference volumes V1-V4 for the individual dispensing cycles and the values relevant for the volumes of the pressure chamber 2 and pressure lines 6, 7 have been entered, the difference values between the respectively assigned first equilibrium pressure and second equilibrium pressure are determined for the individual measurement chambers 10, and a value for an actual volume is associated with each difference value.

A volume can also be assigned to the first equilibrium pressure and second equilibrium pressure and the difference of these volume values is determined to determine the actual volume.

The allocation of a pressure value to a volume value will be described more fully following the description of the process.

After determining the actual volumes, the actual volumes are compared to the reference volumes V1-V4 and/or the actual volumes are compared to one another, and the volume deviations are determined.

8th Process Step:

When the determined volume deviations lie outside a predetermined tolerance, the parameters of the liquid handling device 18 influencing the respective dispensing volume are changed. For example, the opening time of the valves of the dispensing channels 19 is changed. The change of parameters can be automated in that values determined for the volume deviations are entered as controlling quantities in a control device 15 which can be connected to the liquid handling device 18.

The determination of a volume value from a measured pressure value is carried out by means of the thermal equation of state of ideal gases $p \cdot V = n \cdot R \cdot T$, where p is pressure, V is volume, T is temperature, and R is the universal gas constant, and the proposition that the amount of gas in the system before and after the pressure equilibrium is constant, i.e., the amount of gas in the measurement chamber 10 plus the amount in the pressure chamber 2 is equal to the amount in the pressure chamber 2 and measurement chamber 10 after equilibrium.

This relationship gives the following equation (Equation 1) for an arrangement according to the invention:

$$\frac{P_{MK} \cdot (V_{MK} + V_L - V_{actual})}{T_{MK}} + \frac{P_{DK} \cdot V_{DK}}{T_{DK}} = \frac{(V_{MK} + V_L + V_{DK} - V_{actual}) \cdot P_{equilibrium}}{T_2},$$

where $V_{MK}$=volume of the measurement chamber 10
$V_{DK}$=volume of the pressure chamber 2 (including the proportional volumes of the pressure lines 6 and 7 between the two valves 3 and 4)
$P_{MK}$=measurement chamber pressure
$P_{DK}$=operating pressure
$P_{equilibrium}$=the first or second equilibrium pressure or the difference value between the first and second equilibrium pressure
$V_{actual}$=volume of the liquid (dispensing volume)
$T_{MK}$=temperature of the gas in the measurement chamber 10
$T_{DK}$=temperature of the gas in the pressure chamber 2
$T_2$=temperature of the gas after equilibrium
$V_L$=proportional volume of the pressure line 7 in the direction of flow behind the valve 4.

In order to reliably determine very small volumes with this measurement principle, the conception of an arrangement according to the invention relied on the state of the art of precision engineering and microsystem technology. It was not possible to realize a measuring device of this kind prior to the use of valves (for example, Bürkert™ Type 127) with very small internal channel volumes and high-resolution microtechnology pressure sensors (for example, Honeywell™ SCX Sensor). The advantage of the construction that has been realized consists in that the ambient pressure, which corresponds to the measurement chamber pressure in the realized construction, can also be measured by the integrated pressure sensor 5 by venting.

In realizing the construction, a special significance is attributed to the thermal behavior of the system. Equality of temperature and constancy during the process of measuring the gas in the pressure chamber 2, the gas in the measurement chamber 10 and the liquid 17 in the measurement chamber 10 are indispensable for the functioning of the measurement principle and for accuracy. This temperature equality and constancy can be ensured economically by the advantageous use of materials with good thermal conducting properties, realization of sufficiently high thermal capacities, and thermal decoupling to the environment. This eliminates a laborious temperature regulation of the measuring device, gas and medium. Further, the measurement is carried out in a time window of 2 to 3 second so that other known diffusion-dependent influences such as solubility in gas and liquid absorption capacity of the measurement gas may be disregarded.

As was already mentioned, instead of entering them into the storing and evaluating unit 14, the values for the reference volumes V1-V4 can also be determined by the arrangement itself in that the arrangement is advantageously calibrated exactly to these reference volumes V1-V4.

In principle, the arrangement can be calibrated without filling with only two reference chambers 11 having different known chamber volumes, or with two reference chambers 11 having identical known chamber volumes, where at least one of the reference chambers 11 must be filled with a known volume of liquid 17, a calibrating volume VK1-VK4. In accordance with the process according to the invention, the equilibrium pressures associated with the reference chambers 11 are measured and assigned to the known volumes. In principle, two values, each of which is assigned to a volume, are sufficient to determine all of the necessary measurement system parameters which make it possible to assign a volume to each of the measurement values or to calculate a volume therefrom. Nevertheless, exact calibration to a plurality of volumes, namely, to those that are actually to be dispensed, may be advantageous for obtaining more accurate results.

It will be appreciated by the person skilled in the field of this invention that the invention is not limited to the particulars of the embodiment forms described above by way of example and that the present invention may be embodied in other specific forms without departing from the scope of the invention as set forth in the accompanying claims.

The calibration of a single-channel liquid handling device 18 to a reference volume V1 based on specific process parameters will be described in the following.

Default parameters:

operating pressure $P_{DK}$=3000 mbar, air pressure or measurement chamber pressure $P_{MK}$=1000 mbar volume of the pressure chamber 2 (including the proportional volumes of the pressure lines 6 and 7 between the two valves 3 and 4) $V_{DK}$=20 μm, reference volume V1=30 μl, proportional volume of the second pressure line 7 behind the valve 4 $V_L$=10 μl, default dispensing valve opening time $t_{old}$=500 ms.

By correcting the opening time t of the dispensing valve, the actual volume is changed until it corresponds to the reference volume V1.

The volume of the measurement chamber 10, which is still unknown, is first determine by similarly working through the process steps 1 to 3 described above. An equilibrium pressure of $P_{equilibrium}$=1571 mbar is measured. Using Equation 1, where $T_{MK}=T_{DK}=T_2$ and $V_{actual}=0$, and converting for $V_{MK}$, the volume of the measurement chamber 10 can now be calculated using Equation 2:

$$V_{MK} = -V_L + \frac{V_{DK}(P_{equilibrium} - P_{DK})}{P_{MK} - P_{equilibrium}}.$$

A volume $V_{MK}$ of 40 μl results in the selected example.

It will be clear to the person skilled in the art that the volume can also be determined by a previously determined calibrating characteristic of the measuring device instead of by calculation.

Process steps 4 and 5 are now carried out.

Following this, the actual volume $V_{actual}$ in a measurement chamber 10 having a measurement chamber volume $V_{MK}$ that is now known is determined.

After the measurement chamber 10 has been filled with the actual volume and process steps 1-4 have been carried out again, a second equilibrium pressure of, e.g., $P_{equilibrium}$=1900 mbar is obtained.

The actual volume of the liquid 17 can now be calculated by Equation 1, where $T_{MK}=T_{DK}=T_2$ and $V_{MK}$=40 ml, and converting by $V_{actual}$:

$$V_{actual} = \frac{P_{equilibrium}(V_{MK} + V_L - V_{DK}) - P_{MK}(V_{MK} + V_L)}{P_{equilibrium} - P_{MK}}.$$

In the selected example, there is an actual volume of 25.6 μl.

Figure 3A:
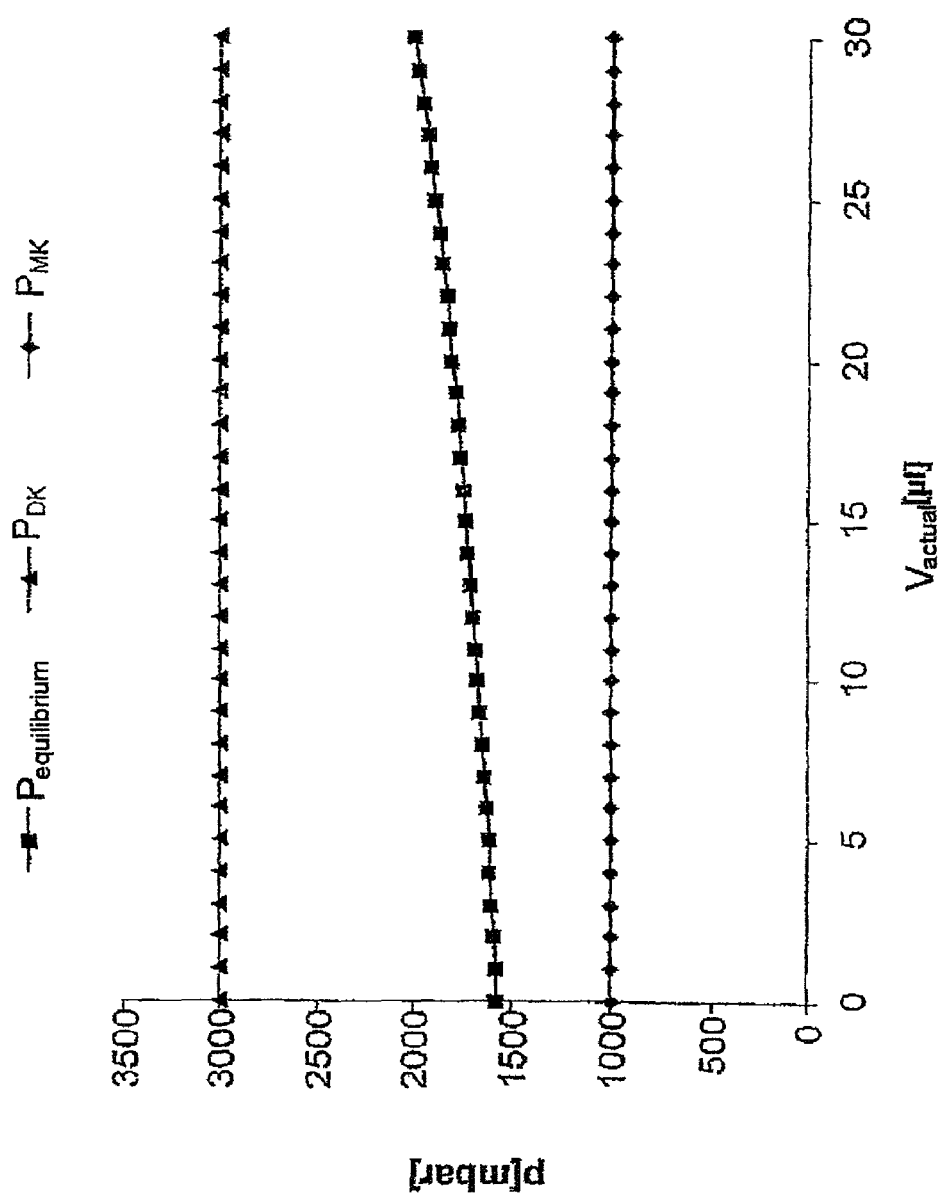
FIG. 3a is a graph showing the dependency of $V_{actual}$ on P.

FIG. 3a shows the relationships between the measured equilibrium pressures and the actual volumes.

In this case, the actual volume can also be determined by means of the previously determined calibrating characteristic.

The liquid handling device 18 can now be calibrated to the reference volume V1 using the determined actual volume. In this case, the new opening time $t_{new}$ of the dispensing valve is determined from the old opening time $t_{old}$ and a factor of the reference volume and actual volume as follows:

$$t_{new} = \frac{t_{old} \cdot V_{reference}}{V_{actual}}.$$

Figure 3B:
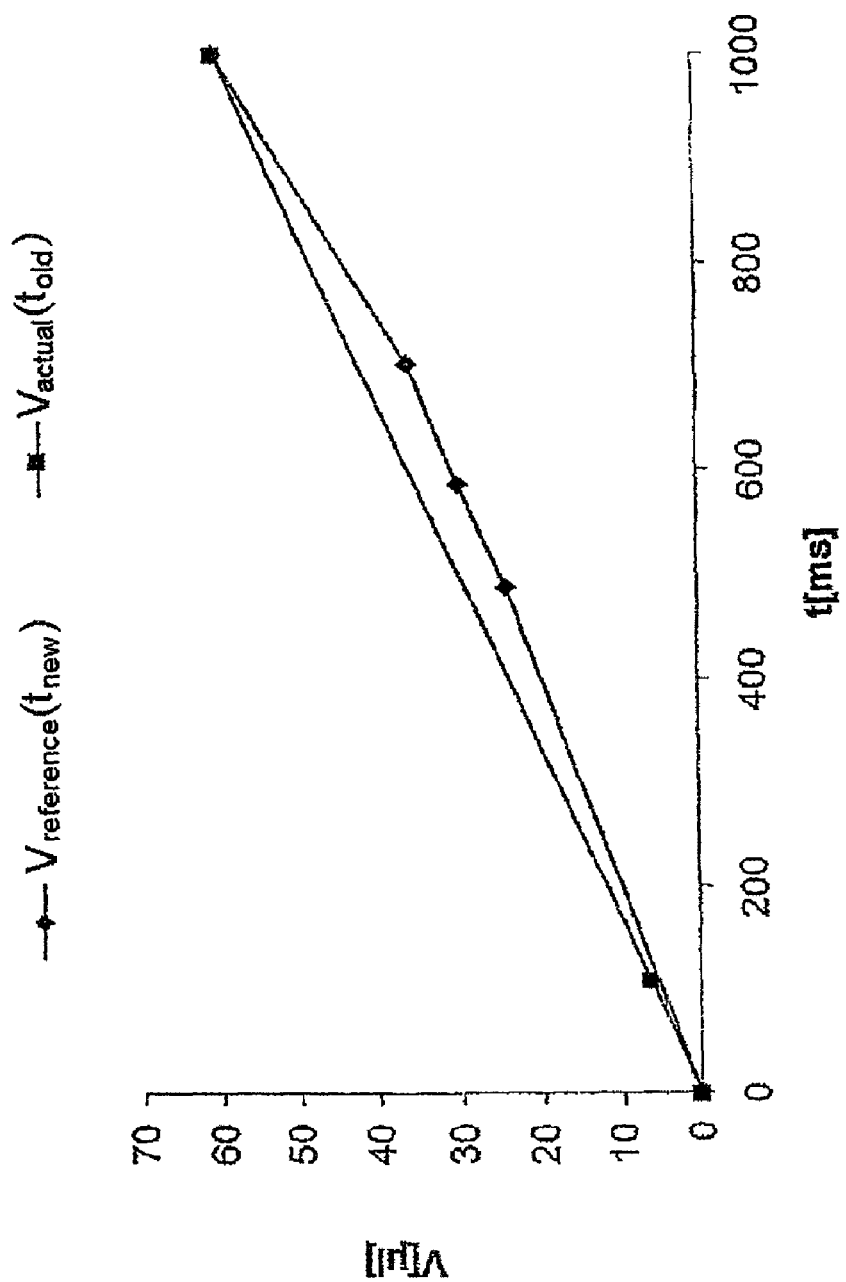
FIG. 3b is a graph showing the dependency of V on t.

In the example, this results in a correction of the opening time from $t_{old}$=500 ms to $t_{new}$=586 ms. FIG. 3b shows the correction of the dispensing characteristic of a dispensing system.

The calibration of a multi-channel dispensing system is carried out by means of a corresponding number of repetitions of the described process steps.

The calibration of the measuring device will now be detailed with reference to a specific embodiment example. The two reference chambers 11 needed for this purpose have different known measurement chamber volumes.

Volume of the first known measurement chamber $V_{MK1}$=40 μl

Volume of the second known measurement chamber $V_{MK2}$=10 μl.

After positioning the first reference chamber 11 beneath the seal 8 and carrying out the pressure equilibrium similar to process steps 1 to 3, an equilibrium pressure of, e.g., $P_{equilibrium}$=1571 mbar is measured and assigned to $V_{MK1}$=40 μl.

After positioning the second reference chamber 11 beneath the seal 8 and carrying out the pressure equilibrium similar to process steps 1 to 3, an equilibrium pressure of, e.g., $P_{equilibrium}$=2000 mbar is measured and assigned to $V_{MK2}$=10 μl.

The relevant parameters $V_L$=10 μl, $V_{DK}$=20 μl of the arrangement can now be determined from the obtained measurement data for the two reference chambers 11 using Equation 1.

It will be clear to the person skilled in the art that it is also possible to generate a calibrating curve which shows the direct relationship between equilibrium pressure and liquid volume.

While the foregoing description and drawings represent the present invention, it will be obvious to those skilled in the art that various changes may be made therein without departing from the true spirit and scope of the present invention.

REFERENCE NUMBERS 1 device for generating an operating pressure
2 pressure chamber
3 input valve
4 output valve
5 pressure sensor
6 first pressure line
7 second pressure line
8 seal
9 measurement chamber carrier
10 measurement chamber
11 reference chamber
12 holder
13 sealing surface
14 storing and evaluating unit
15 control unit
16 3D coordinate table 17 liquid
18 liquid handling device
19 dispensing channel
VK1-VK4 calibrating volume
K1-K8 measurement chamber assigned to a determined dispensing channel
V1-V4 reference volume per dispensing cycle

What is claimed is:

1. A process for calibrating and/or equilibrating single-channel and multi-channel liquid handling devices in which a dispensing volume of a liquid is dispensed in a measurement chamber of a measurement chamber carrier via dispensing channel(s) of the liquid handling device, each measurement chamber being associated with a dispensing channel, and the dispensing volumes which correspond in each instance to an actual volume are determined in the individual measurement chambers and compared to a reference volume and/or to one another in order to change device parameters influencing the respective dispensing volume in the event of deviations beyond a predetermined tolerance limit, comprising the following process steps:

generating an operating pressure in a pressure chamber whose volume is known;
hermetically sealing an unfilled measurement chamber and connecting the measurement chamber to the pressure chamber;
measuring the chamber pressure, which is now equal to a first equilibrium pressure that has undergone a pressure change relative to the operating pressure depending on the measurement chamber volume;
storing the first equilibrium pressure associated with this measurement chamber;
opening the measurement chamber and repeating the preceding process steps depending on the quantity of additional measurement chambers in the measurement chamber carrier;
filling the measurement chambers by dispensing a liquid via the dispensing channels of the liquid handling device;
generating the operating pressure in the pressure chamber;
hermetically sealing a measurement chamber and connecting this measurement chamber to the pressure chamber;
measuring the chamber pressure, which is now equal to a second equilibrium pressure that has undergone a pressure change relative to the operating pressure depending on the difference between the measurement chamber volume and the liquid volume;
storing the second equilibrium pressure associated with this measurement chamber;
opening the measurement chamber and repeating the preceding three process steps depending on the quantity of additional measurement chambers in the measurement chamber carrier;
determining difference values between the first and second equilibrium pressures associated in each instance with a measurement chamber;
associating individual actual volume values with the individual difference values using the thermal equation of states of ideal gases $p \cdot V = n \cdot R \cdot T$, where p is pressure, V is volume, T is temperature, and R is the universal gas constant, and the proposition that the amount of gas in the system before and after the pressure equilibrium is constant, i.e., the amount of gas in the measurement chamber plus the amount in the pressure chamber is equal to the amount in the pressure chamber and measurement chamber after equilibrium;
comparing these actual volume values in each instance to a value for a reference volume and/or to one another; and
changing the device parameters of the liquid handling device influencing the dispensing volumes are changed in the event of deviations of the actual volume values from the value for the reference volume or from one another beyond a predetermined tolerance and, if necessary, repeating the preceding process steps beginning with the filling of the measurement chambers.

2. The process according to claim 1;
wherein an arrangement used for carrying out the process is calibrated at the start of the measuring process in that a first equilibrium pressure is determined for two reference chambers with different known volumes and the pressure chamber volume is derived from their difference.

3. The process according to claim 1;
wherein an arrangement used for carrying out the process is calibrated at the start of the measuring process in that an equilibrium pressure is determined according to claim 1 for two unfilled reference chambers having different known chamber volumes.

4. An arrangement for calibrating and/or equilibrating single-channel and multi-channel liquid handling devices comprising:

a measurement chamber carrier having one or more measurement chambers with openings on one side and arranged in a grid;
each of the openings lying in a plane and where grid spacing is adapted, if necessary, to grid spacing of the dispensing channels of the liquid handling device to be calibrated and/or equilibrated; and
a storing and evaluating unit in which relevant measurement values for the dispensing volumes of a liquid dispensed to the measurement chambers via the dispensing channels corresponding in each instance to an actual volume are formed so as to be associated with the measurement chambers and stored and compared to a value for reference volumes and/or to one another in order to determine tolerance deviations of the dispensing volumes, and a control unit which is connected to the storing and evaluating unit for changing influential device parameters if necessary; and further comprising:
a pressure chamber being provided and being connected on the input side by a first pressure line to a device for generating an operating pressure and communicating on an output side by a second pressure line with a seal which surrounds the free end of the pressure line;
an inlet valve being provided for opening and closing the first pressure line and an outlet valve being provided for opening and closing the second pressure line;
a pressure sensor by which the chamber pressure in the pressure chamber can be measured being connected to the pressure chamber;
a holder being provided in which the measurement chamber carrier is arranged, and a sealing surface of the seal lying parallel to the plane of the opening of the measurement chambers, which sealing surface is larger than the opening of a measurement chamber;
means for horizontal relative movement between the measurement chamber carrier and the seal being provided to position the measurement chambers successively beneath the seal;
means for the vertical relative movement between the measurement chamber carrier being arranged in the holder and the seal being provided to periodically hermetically seal a measurement chamber located beneath the seal relative to the environment and to connect the measurement chamber to the pressure chamber; and said pressure sensor and said means for relative movement being connected to the storing and evaluating unit.

5. The arrangement according to claim 4;

wherein the control device which is connected to the storing and evaluating unit has an interface to which a liquid handling device to be calibrated and/or equilibrated can be connected is provided for automatically calibrating and/or equilibrating the liquid handling device.

6. The arrangement according to claim 4;

wherein the measurement chamber carrier is a microtitration plate and the measurement chambers are formed by the wells of the latter.

7. The arrangement according to claim 4;

wherein the measurement chambers are cells, cell culture trays or reaction vessels.

8. A process for calibrating and/or equilibrating single-channel and multi-channel liquid handling devices in which a dispensing volume of a liquid is dispensed in a measurement chamber of a measurement chamber carrier via dispensing channels of the liquid handling device, each measurement chamber being associated with a dispensing channel, and the dispensing volumes which correspond in each instance to an actual volume are determined in the individual measurement chambers and compared to a reference volume and/or to one another in order to change the device parameters influencing the respective dispensing volume in the event of deviations beyond a predetermined tolerance limit, comprising the following process steps:

generating an operating pressure in a pressure chamber whose volume is known;

hermetically sealing an unfilled measurement chamber and connecting the measurement chamber to the pressure chamber;

measuring the chamber pressure, which is now equal to a first equilibrium pressure that has undergone a pressure change relative to the operating pressure depending on the measurement chamber volume;

associating an individual actual volume value with the first equilibrium pressure using the thermal equation of states of ideal gases $p \cdot V = n \cdot R \cdot T$, where p is pressure, V is volume, T is temperature, and R is the universal gas constant, and the proposition that the amount of gas in the system before and after the pressure equilibrium is constant, i.e., the amount of gas in the measurement chamber plus the amount in the pressure chamber is equal to the amount in the pressure chamber and measurement chamber, and storing the first actual volume value associated with this measurement chamber;

opening the measurement chamber and repeating the preceding process steps depending on the quantity of additional measurement chambers in the measurement chamber carrier;

filling the measurement chambers by dispensing a liquid via the dispensing channels of the liquid handling device;

generating the operating pressure in the pressure chamber;

hermetically sealing a measurement chamber and connecting this measurement chamber to the pressure chamber;

measuring the chamber pressure, which is now equal to a second equilibrium pressure that has undergone a pressure change relative to the operating pressure depending on the difference between the measurement chamber volume and the liquid volume;

associating an individual actual volume value with the second equilibrium pressure using the thermal equation of states of ideal gases $p \cdot V = n \cdot R \cdot T$, where p is pressure, V is volume, T is temperature, and R is the universal gas constant, and the proposition that the amount of gas in the system before and after the pressure equilibrium is constant, i.e., the amount of gas in the measurement chamber plus the amount in the pressure chamber is equal to the amount in the pressure chamber and measurement chamber, and storing the second actual volume value associated with this measurement chamber;

opening the measurement chamber and repeating the preceding three process steps depending on the quantity of additional measurement chambers in the measurement chamber carrier;

determining difference values between the first actual volume value and the second actual volume value associated in each instance with a measurement chamber;

comparing these difference values in each instance to a value for a reference volume and/or to one another; and changing the device parameters of the liquid handling device influencing the dispensing volumes are changed in the event of deviations of the difference values from the values for the reference volumes or from one another beyond a predetermined tolerance and, if necessary, repeating the preceding process steps beginning with the filling of the measurement chambers.

9. The process according to claim 8;

wherein an arrangement used for carrying out the process is calibrated at the start of the measuring process in that a first equilibrium pressure is determined for two reference chambers with different known volumes and the pressure chamber volume is derived from their difference.

10. The process according to claim 8;

wherein an arrangement used for carrying out the process is calibrated at the start of the measuring process in that an equilibrium pressure is determined according to claim 8 for two unfilled reference chambers having different known chamber volumes.

* * * * *